United States Patent [19]

Pinto et al.

[11] Patent Number: 4,858,277
[45] Date of Patent: Aug. 22, 1989

[54] PROCESS AND APPARATUS FOR CLEANING AND OPENING LOOSE FIBER STOCK, E.G. COTTON

[75] Inventors: Akiva Pinto, Duesseldorf; Guenter Lucassen, Haltern; Heinz Dirkes, Telgte, all of Fed. Rep. of Germany

[73] Assignee: Hergeth Hollingsworth GmbH, Duelman, Fed. Rep. of Germany

[21] Appl. No.: 246,466

[22] Filed: Sep. 19, 1988

[30] Foreign Application Priority Data

Oct. 9, 1987 [DE] Fed. Rep. of Germany ....... 3734145

[51] Int. Cl.⁴ .......................... D01B 3/00; D01B 1/00
[52] U.S. Cl. ........................................ 19/200; 19/205; 19/105; 364/470
[58] Field of Search ...................... 19/65 A, 65 R, 105, 19/200, 204, 205, 224, 239, 240, 300, 304–308; 364/470 R

[56] References Cited

U.S. PATENT DOCUMENTS

| | | | |
|---|---|---|---|
| 3,256,569 | 6/1966 | Draving | 19/105 X |
| 3,562,866 | 2/1971 | Roberson et al. | 19/105 X |
| 3,892,951 | 7/1975 | Stutz | 364/470 R |
| 3,984,896 | 10/1976 | Hicks | 19/200 X |
| 4,167,803 | 9/1979 | Teichmann | 19/105 X |
| 4,512,060 | 4/1985 | Shofner | 19/200 |
| 4,631,781 | 12/1986 | Shofner | 19/200 |

Primary Examiner—Donald Watkins
Attorney, Agent, or Firm—Cort Flint

[57] ABSTRACT

A process and apparatus is disclosed for cleaning and opening loose fiber material which is fed through a feeder to a cleaning operation to be carried away for further processing. The degree of contamination of the fiber material is concurrently scanned. Control of the cleaning procedure is performed in response to the scanned measuring results. A measuring path is provided between a fiber feeder (2) and an opening and cleaning unit (3). At the measuring path (24), there is arranged a device (300) for scanning the degree of contamination of the fiber material. A controller (41) controls cleaning unit (3) and/or take-off rolls (8, 9) of feeder (2). The control of the cleaning procedure is relatively instantaneous in accordance wit the result of a proceeding measurement of the degree of contamination of the fiber material.

20 Claims, 1 Drawing Sheet

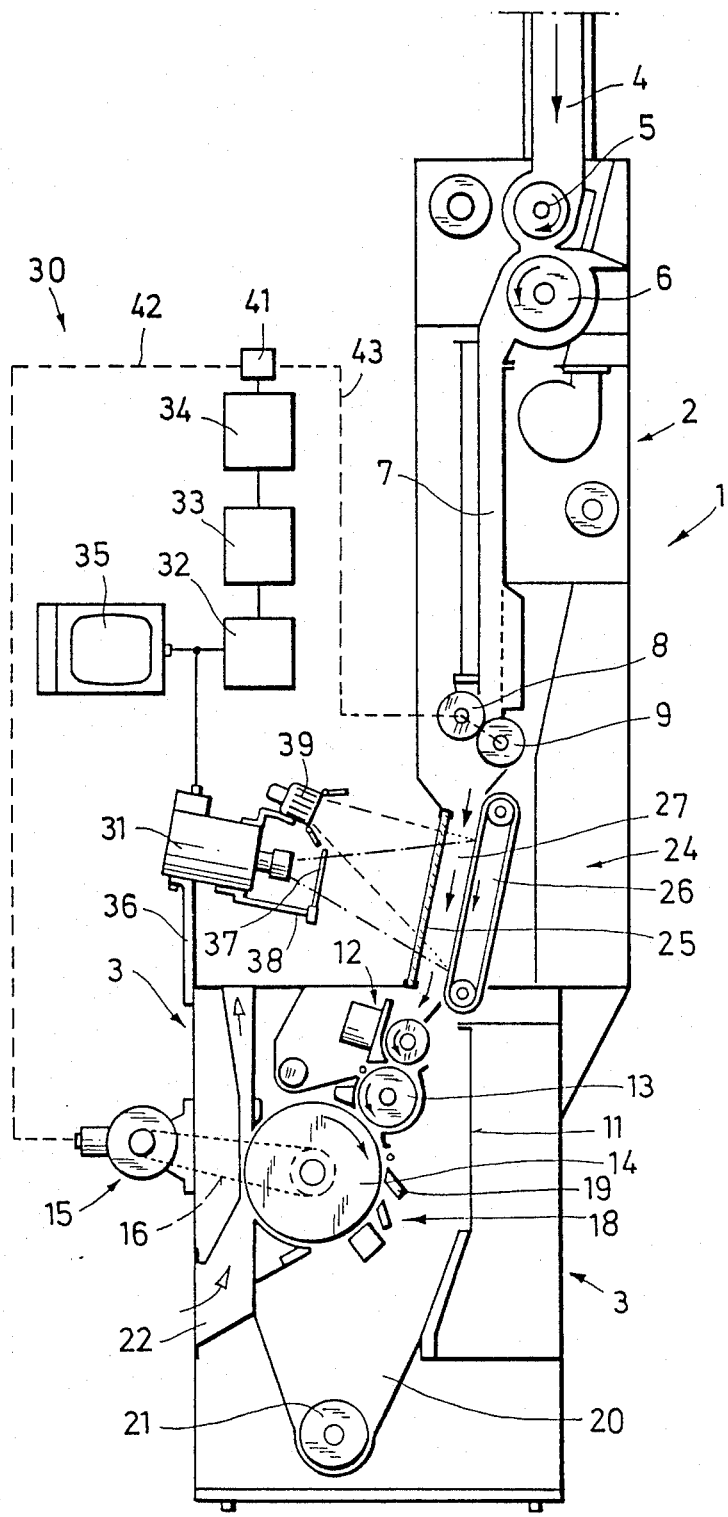

PROCESS AND APPARATUS FOR CLEANING AND OPENING LOOSE FIBER STOCK, E.G. COTTON

BACKGROUND OF THE INVENTION

The invention relates to a process and apparatus for cleaning and opening loose fiber stock like cotton, synthetic fibers, etc. The fiber material is passed through a feeder and afterwards is subjected to a cleaning operation to be further processed.

It is customary with cleaning means which prepare textile fiber material for cards, etc., to feed the fiber material by means of a chute feed and the like to intake rollers of the opening and cleaning unit. The cleaning unit by itself comprises one or more opening and cleaning rollers which cooperate with knife blades and the like. The cleaned fiber material moves to a collecting chamber from where it is carried away pneumatically. To ensure efficient operation of the cleaning means, samples of the fiber material fed thereto are taken from time to time to test for their extent of contamination. Subject to the degree of contamination, the cleaning means is reset, on the basis that the extent of contamination has changed. The operation is substantially intermittent. The scanning of the sample contamination takes a certain time, and the resetting of cleaning means based on the detected result is somewhat delayed. The degree of contamination of the fiber material subsequently fed may have changed meanwhile producing an unsatisfactory result.

Quality of the cleaned fiber material is considerably affected by this situation and may vary impairing the processing operation at the card.

Accordingly, an object of the invention is to substantially improve and perform more reliably cleaning of textile fiber material and adjust for degree of contamination in preparation for processing the material on a textile card or other textile processing equipment.

SUMMARY OF THE INVENTION

The invention is characterized in that the contamination of the fiber material is continuously determined during its feeding to a cleaning unit and a direct control of the cleaning operation is performed in response to a measured contamination. The cleaning of the fiber material by the cleaning unit may be substantially improved and homogenized. The control of the cleaning operation corresponds to the result of an immediately preceding contamination measurement made with the fiber material. The control of the cleaning operation in response to the measured contamination of fiber material is essentially instantaneous. By this means, the quality of the cleaned textile fiber material fed from the cleaning unit to a card is considerably improved. The degree of cleaning is more uniform with a resultant favorable effect on the further processing of the spinning material on a card and the like, including the final product. At the same time, an increase in output of the cleaning unit ma be achieved.

According to another feature of the invention, the degree of contamination of the fiber material is preferably scanned by optical-electronic means. The measured contamination values may be input into a process computer by which the cleaning operation at the cleaning unit is controlled through a control current. A highly accurate cleaning operation is obtained whereby the uniformity of the cleaning is substantially provided.

The invention is suitably realized by providing a measuring path for the passing fiber material between a fiber feeder and an intake of the opening and cleaning unit. At the measuring path, a means for scanning the degree of contamination of the fiber material is provided for the control of the cleaning unit. Preferably, the measuring path may be a channel-type guide. To this effect, the guide is composed of a conveying means and of a sliding surface confronted therewith. This configuration does not noticeably influence the supply of the fiber material from a chute feed or supply box to the cleaning means. Care is taken only that the fiber material moves as a layer having a nearly uniform thickness in the measuring path. During the transport, conveying means, in the form of a conveyor belt, somewhat urges the fiber layer against the sliding surface. This supports continuous transport of the fiber material in the measuring path.

Preferably, the slide surface is a transparent plate, e.g. of glass or the like. It is further suitable for the conveyor belt to be colored brightly or to be transparent in order to optimize scanning of the degree of contamination of the fiber material. As to the scanning of contamination of the fiber material, the respective apparatus may comprise means suited for the desired purpose. Advantageously, the apparatus comprises a camera, preferably a television camera, a grey value comparator, a counter, and a computer. By means of cooperating units, the degree of contamination of the fiber layer passing by the slide surface may be detected quickly and reliably converted into a control signal. A respective filter may be connected supplementarily to the camera in view of an expanded contrast. A control unit is connected via control lines to the drive for the cleaning roller(s) of the cleaning unit and/or the take off rollers of the chute feed.

DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

The Figure shows a schematic elevation of an embodiment of a cleaning and opening unit according to the invention in combination with a chute feed.

DESCRIPTION OF A PREFERRED EMBODIMENT

Referring now in more detail to the drawing, an apparatus, designated generally as 1, is disclosed for the controlled cleaning of textile fiber material. The apparatus is composed of a chute feed 2 and a cleaning and opening means 3. Chute feed 2 comprises a reserve box 4 followed by an opening means comprising rollers 5 and 6. Roller 6 may be a beater or opening roller. The fiber material is conveyed into a feeder box 7 in which the fiber material is compacted mechanically or by means of an air current. At the lower end of the feeder box 7, there are fiber take off rollers 8 and 9.

Cleaning and opening means 3 comprises a housing 11 in which an intake means 12, an intermediate roller 13 and an opening roller 14 are pivotally supported. Opening roller 14 is driven by a motor 15 and a transmission member 16. The cleaning and opening roller 14 cooperates with cleaning means 18 which may consist of one or a plurality of successive blades 19. Waste from cleaning means 18 may be collected in a closed funnel-shaped housing section 20 to be discharged, preferably pneumatically, through a tube 21. At the rear side of the opening roller 14, there is conveniently arranged a suction channel 22 disposed tangentially to the roller and serving for carrying away the cleaned material.

Between feeder 2 and cleaning and opening means 3, is normally provided a chute along which the fiber material is transported from feeder 2 to cleaning and opening means 3. In accordance with the invention, this section is used as a measuring path for scanning the degree of contamination of the fiber material passing therethrough. Measuring path 24 is composed of a slide surface 25, and a conveyor means 26, e.g. a conveyor belt which forms a channel-type guide 27. For the instant purpose, the slide surface 25 is a transparent plate of glass or the like. The conveyor means 26 serves for the continuous advance movement of the fiber material through channel-type guide 27, on the one hand, and for urging the fiber layer in the channel 27 against plate 25, on the other hand.

The means 30 for scanning the degree of contamination of the fiber material moving through the channel-type guide 27 comprises a camera 31 (diode line camera, television camera), a grey value comparator 32, a counter 33, and a process computer 34. A monitor 35 may be interconnected. The camera 31 may be secured to a mounting 36 and is directed to the transparent plate 25. Further, camera 31 may be fitted with a supplementary optical filter for expanded contrast. The filter is carried by mounting 38. Suitably, a lamp 39 serves for lightening the picture to be taken at the transparent plate 25. To this effect, the surface of conveyor belt 26 should be bright.

A control assembly 41 receives measured contamination values from computer 34 to control drive 15 for cleaning roller 14 via control line 42 and the drive for take off rollers 8, 9 by means of control line 43. The distance between the transparent plate 25 and the conveyor belt 26 preferably ranges between 2 to 4 cm. As a rule, the distance may be about 3 cm. The continuous scanning of the degree of contamination of the fiber layer moving through the measuring path by the camera, and the immediate determination evaluation by the counter and the computer of the contamination of the fiber material, provide an immediate detection changes in the contamination of the fiber material. The opening and cleaning operation may be controlled in response to immediately measured fiber material without delay.

During the contactless measuring, the object to be measured is imaged via a lens on a line sensor, e.g. a diode line camera. The brightness information on the sensor is converted into electric signals and prepared for the processing by a computer which is responsible for the evaluation of the image information, e.g. the dimensional analysis of the imaged object. The scanning, measured contamination signal generation, and control of the take-off rolls and/or intake rolls may be done with classical techniques as is well within the purview of one skilled in the automatic programmer and control art.

While a preferred embodiment of the invention has been described using specific terms, such description is for illustrative purposes only, and it is to be understood that changes and variations may be made without departing from the spirit or scope of the following claims.

What is claimed is:

1. A process for cleaning and opening loose fiber material of the type which includes feeding said fiber material through a feeder to a cleaning operation, and conveying said fiber material away from said cleaning operation for further fiber material processing, wherein said process comprises continuously scanning the degree of contamination of said fiber material, while said fiber material is fed to the cleaning operation, generating a signal representing a measured degree of contamination of said scanned fiber material, and controlling said cleaning operation in response to said signal representing said measured degree of contamination.

2. The process of claim 1 including scanning the degree of contamination of fiber material by using an optical-electrical means for measuring said degree of contamination and generating said signal, and processing said signal in a computer which controls said cleaning operation in response to said signal.

3. The process of claim 1 including conveying said fiber material through a channel between said fiber feeder and said cleaning operation, and scanning and measuring said degree of contamination while said fiber material is passing through said channel.

4. The process of claim 3 including conveying said fiber material through a channel which has a transparent outer plate through which said fiber material may be visually and electronically scanned.

5. In an apparatus for cleaning and opening loose textile fiber material, the combination comprising a fiber feeder having take-off rolls, opening and cleaning means having intake means for receiving fibers from said fiber feeder, and means for discharging the fiber material from said opening and cleaning means, a measuring channel disposed between said fiber feeder and said opening and cleaning means through which fibers are fed from said fiber feeder to said opening and cleaning means; scanner means for measuring a degree of contamination of said fiber material passing through said fiber channel, and control means for controlling said opening and cleaning means in response to said scanner means and the degree of contamination of said fiber material.

6. The apparatus of claim 5 wherein said fiber channel is defined between a conveyor means and a slide surface.

7. The apparatus of claim 6 including illumination means for illuminating said slide surface.

8. The apparatus of claim 6 wherein said slide surface constitutes the front of said fiber channel and consists of a transparent plate.

9. The apparatus of claim 8 wherein said conveyor means includes a conveyor belt which urges fiber material passing through said channel against said transparent plate.

10. The apparatus of claim 8 wherein said conveyor means includes a conveyor belt which urges said fiber material passing through said channel against said slide surface and said conveyor belt has a surface which is brilliant.

11. The apparatus of claim 9 wherein said conveyor belt has a surface which is transparent.

12. The apparatus of claim 5 wherein said scanning means comprises a camera means, a gray value comparator, a counter, and a computer, connected in order for processing and generating said signal.

13. The apparatus of claim 11 including a monitor connected between said camera and said comparator.

14. The apparatus of claim 5 wherein said control means comprises control lines connected to said take-off means of said feeder and to said intake means of said opening and cleaning means.

15. Apparatus for cleaning and opening loose textile fibers of the type which includes a chute feeder having fiber take-off rolls, fiber opening and cleaning means having the fiber intake means, and a means for discharging the fiber material from said opening and cleaning means wherein the improvement comprises a measuring channel disposed between said take-off means of said chute feeder and said intake means of said opening and cleaning means, scanning means for measuring contamination in said fiber material passing through said measuring channel, and control means for controlling the delivery of fiber material of through said opening and cleaning means in response to said measured contamination.

16. The apparatus of claim 15 wherein said control means controls said take-off means of said chute feeder.

17. The apparatus of claim 16 wherein said control means controls said intake means of said opening and cleaning means.

18. The apparatus of claim 15 wherein said control means controls said intake means of said opening and cleaning means.

19. The apparatus of claim 15 wherein said measuring channel includes a slide surface against which said fiber material passes as it is fed from said chute feeder to said opening and cleaning means, said scanning means measuring said contamination through said slide surface.

20. The apparatus of claim 19 wherein said slide surface is transparent.

* * * * *